(12) United States Patent
Sharp et al.

(10) Patent No.: US 10,139,104 B2
(45) Date of Patent: Nov. 27, 2018

(54) HAND HELD FLOW-THROUGH STEAM SYSTEM

(71) Applicant: Integrated Medical Systems International, Inc., Birmingham, AL (US)

(72) Inventors: Gregory Sharp, Birmingham, AL (US); Lloyd Starks, Chattanooga, TN (US)

(73) Assignee: STERIS Instrument Management Services, Inc., Birmingham, AL (US)

( * ) Notice: Subject to any disclaimer, the term of this patent is extended or adjusted under 35 U.S.C. 154(b) by 0 days.

(21) Appl. No.: 15/171,995

(22) Filed: Jun. 2, 2016

(65) Prior Publication Data
US 2017/0350587 A1    Dec. 7, 2017

(51) Int. Cl.
| | |
|---|---|
| *F22B 27/04* | (2006.01) |
| *F22B 21/02* | (2006.01) |
| *F22B 29/02* | (2006.01) |
| *F24H 9/00* | (2006.01) |
| *F24H 1/06* | (2006.01) |

(52) U.S. Cl.
CPC .............. *F22B 27/04* (2013.01); *F22B 21/02* (2013.01); *F22B 29/02* (2013.01); *F24H 1/06* (2013.01); *F24H 9/0015* (2013.01)

(58) Field of Classification Search
CPC .......... F22B 27/04; F22B 21/02; F22B 29/02; F24H 1/06; F24H 9/0015; A61L 2/07; A61L 2/186; A61L 2/202; A61L 2/206; A61L 2/208; A61L 2/26; A61L 2/24; A61L 2202/122; A61L 2202/17; A61L 2202/24; B08B 3/08; B08B 3/12; B08B 2230/01

USPC ............ 392/399; 134/57 R, 198, 56 R, 58 R, 134/95.1; 422/28, 292
See application file for complete search history.

(56) References Cited

U.S. PATENT DOCUMENTS

| | | | | |
|---|---|---|---|---|
| 4,281,674 A * | 8/1981 | Tanaka | ................... | A61B 1/123 134/170 |
| 7,061,597 B2 * | 6/2006 | Oberleitner | ............ | A01N 37/16 356/135 |
| 7,946,752 B2 * | 5/2011 | Swartz | ............... | A47G 19/2205 366/243 |
| 8,152,361 B2 * | 4/2012 | Swartz | ............... | A47G 19/2205 366/243 |
| 8,529,119 B2 * | 9/2013 | Swartz | ............... | A47G 19/2205 366/243 |
| 8,585,832 B2 * | 11/2013 | Lin | .......................... | A61L 2/07 134/198 |

(Continued)

*Primary Examiner* — Eric Stapleton
(74) *Attorney, Agent, or Firm* — C. Brandon Browning; Maynard, Cooper & Gale, PC

(57) ABSTRACT

A hand held steamer having a housing with an opening for injecting steam into an interior of the housing. A core is positioned in the interior of the housing. The core has holes for receiving the steam into an interior of the core. Spacers center the core within the interior of the housing, thereby forming a chamber in the interior of the housing around an exterior of the core. A device in need of sanitization can be placed in the interior of the core. A source of dry vapor steam is attached to the opening in the housing and the steam is injected into the interior of the housing, around the exterior of the core, and into the interior of the core. The steam sanitizes the surface of the device without damaging the rest of the device, as a result of uniform distribution of steam around the device.

20 Claims, 4 Drawing Sheets

(56) References Cited

U.S. PATENT DOCUMENTS

| | | | | |
|---|---|---|---|---|
| 9,089,239 B2* | 7/2015 | Billadeau | | A47J 31/005 |
| 2005/0025686 A1* | 2/2005 | Sargent | | A61L 2/10 |
| | | | | 422/300 |
| 2005/0274403 A1* | 12/2005 | Lin | | B08B 3/00 |
| | | | | 134/105 |
| 2007/0056447 A1* | 3/2007 | Swartz | | A47G 19/2205 |
| | | | | 99/287 |
| 2007/0207074 A1* | 9/2007 | Jethrow | | A61L 2/04 |
| | | | | 422/292 |
| 2007/0212278 A1* | 9/2007 | Jethrow | | A61L 2/04 |
| | | | | 422/292 |
| 2010/0036357 A1* | 2/2010 | Bala | | A61L 2/28 |
| | | | | 604/404 |
| 2010/0068123 A1* | 3/2010 | Edwin | | B01J 8/003 |
| | | | | 423/447.2 |
| 2010/0263549 A1* | 10/2010 | Lee | | A47J 31/18 |
| | | | | 99/319 |
| 2011/0192845 A1* | 8/2011 | Swartz | | A47G 19/2205 |
| | | | | 220/212 |
| 2012/0080062 A1* | 4/2012 | Parker | | B44D 3/006 |
| | | | | 134/198 |
| 2012/0167773 A1* | 7/2012 | Swartz | | A47G 19/2205 |
| | | | | 99/287 |
| 2013/0032182 A1* | 2/2013 | Collins | | H01L 21/67051 |
| | | | | 134/198 |
| 2013/0078140 A1* | 3/2013 | Stratman | | A61L 2/26 |
| | | | | 422/3 |
| 2014/0044837 A1* | 2/2014 | Weisman | | A47G 19/16 |
| | | | | 426/79 |
| 2014/0242240 A1* | 8/2014 | Billadeau | | A47J 31/20 |
| | | | | 426/435 |
| 2016/0135638 A1* | 5/2016 | Parazynski | | A23F 3/18 |
| | | | | 426/435 |
| 2016/0262565 A1* | 9/2016 | Beckman | | A47J 31/0636 |
| 2016/0296058 A1* | 10/2016 | Hauser | | A47G 19/16 |

* cited by examiner

HAND HELD FLOW-THROUGH STEAM SYSTEM

FIELD OF THE INVENTION

The present invention relates to sanitization or deactivation of medical, dental, pharmaceutical, veterinary or mortuary instruments and devices, and more particularly, to a method and apparatus for deactivating items using steam that selectively heats the surface of the devices.

BACKGROUND OF THE INVENTION

Medical, dental, pharmaceutical, veterinary or mortuary instruments and devices are routinely exposed to blood or other body fluids during medical procedures. Following such procedures, a thorough cleaning and anti-microbial deactivation of the instruments is required before subsequent use. After the device has been washed it is decontaminated, which typically comprises a brief contact with a decontaminating agent such as bleach or steam sufficient to kill the most dangerous pathogens such as hepatitis. Liquid microbial deactivation systems are now widely used to clean and deactivate instruments and devices that cannot withstand the high temperature of a steam deactivation system, such as endoscopes. Liquid microbial deactivation systems typically operate by exposing the medical devices and/or instruments to a liquid disinfectant or a deactivation composition, such as peracetic acid or some other strong oxidant. In such systems, the instruments or devices to be cleaned are typically placed within a deactivation chamber within the deactivation system, or in a container that is placed within the deactivation chamber. During a deactivation cycle, a liquid disinfectant is then circulated through the deactivation chamber. The instruments may then be safely handled for inspection and processed for sterilization. However, it would be faster and cheaper to use steam for decontamination and deactivation if the steam could be applied in a manner that would not damage the instruments.

SUMMARY OF THE INVENTION

The present invention is a hand held steamer which includes a housing having a first end and a second opposite end and an opening for injecting steam into an interior of the housing. A core having a first end and a second opposite end and a plurality of holes for receiving the steam into an interior of the core is positioned in the interior of the housing. Spacers center the core within the interior of the housing, thereby forming a chamber in the interior of the housing around an exterior of the core. A cap is at the first end of the housing and a cap is at the second opposite end of the housing. One of the spacers is reversibly attached to the cap at the first end of the housing and another of the spacers is reversibly attached to the cap at the second opposite end of the housing. The one of the spacers fits reversibly over the first end of the core and the another of the spacers fits reversibly over the second opposite end of the core. The one of the spacers is attached to the cap by means of threads and the another of the spacers is attached to the cap by means of a threaded locking member. The holes in the core may be oriented at an angle relative to a longitudinal axis of the core. The steamer may also be constructed in two segments wherein the two segments are joined by one or more connecting members so that the steamer can be opened and closed along its length.

An advantage of the steamer of the present invention is that it can deliver dry vapor steam continuously along the length of a device, such as a endoscope, and the steam temperature can be adjusted by adjusting the steam pressure.

Another advantage is that the steamer obviates the need for liquids to sanitize and decontaminate devices.

Another advantage is a steamer that sanitizes and decontaminates devices quicker and cheaper than existing devices and methods.

Another advantage is a steamer that has a middle area that acts as a baffle so that the steam sanitizes and decontaminates the surface of a device without damaging the rest of the device, as a result of uniform distribution of steam around the device.

Another advantage is a steamer that is easy to assemble and to disassemble for maintenance.

DETAILED DESCRIPTION OF THE INVENTION

While the following description details the preferred embodiments of the present invention, it is to be understood that the invention is not limited in its application to the details of construction and arrangement of the parts illustrated in the accompanying FIGURES, since the invention is capable of other embodiments and of being practiced in various ways.

Figure 1:
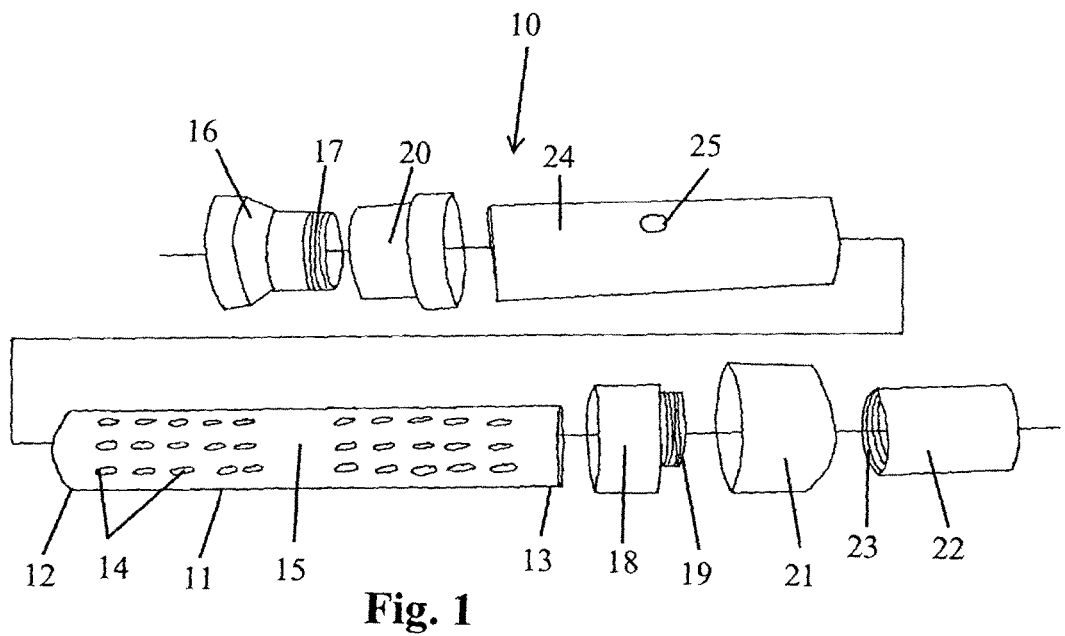
FIG. 1 shows an exploded side perspective view of the hand held flow-through steamer of the present invention.

FIG. 1 shows an exploded side perspective view of the hand held flow-through steamer 10 of the present invention. The steamer 10 has a hollow core 11 having a first end 12 and a second opposite end 13. Core 11 has a plurality of holes 14 except in a middle area 15 which can have no holes 14. A hollow spacer 16, having threads 17, fits reversibly over the first end 12 of core 11 and is reversibly attached to a cap 20 by means of threads 26 in cap 20 (see FIG. 7). A hollow spacer 18, having threaded portion 19, fits reversibly over the second opposite end 13 of core 11. A cap 21 fits over the spacer 18 and the threaded portion 19 extends through the cap 21. A hollow locking member 22 having threads 23 attaches to the threaded portion 19 and locks the spacer 18 to the cap 21. When the core 11 is inserted into a housing 24 the cap 20 fits over one end of the housing 24 and the cap 21 fits over an opposite end of the housing. The housing 24 has a hole 25 through which steam is introduced.

Figure 2:
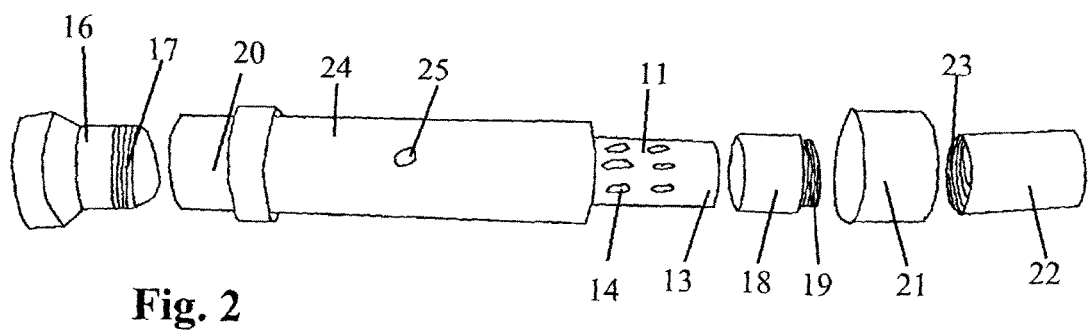
FIG. 2 shows a side perspective view of partial assembly of the steamer with a core partially inserted within a housing and a cap positioned on a one end of the housing.
Figure 3:
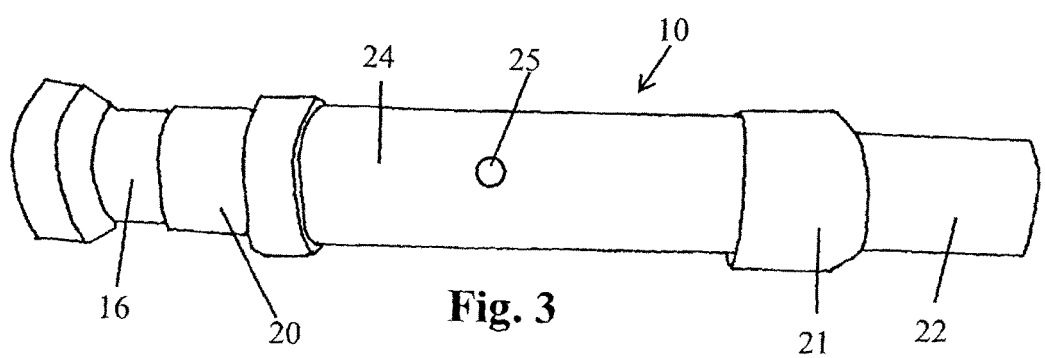
FIG. 3 shows a side perspective view of an assembled steamer.

FIG. 2 shows a partial assembly of the steamer 10 with a core 11 partially inserted within the housing 24. The cap 20 is positioned on one end of the housing. FIG. 3 shows an assembled steamer 10 with the cap 20 positioned on one end of the housing 24 and cap 21 positioned on an opposite end of the housing 24. Spacer 16 is connected to a cap 20 and locking member 22 is connected to spacer 18. The caps 20 and 21 are reversibly attached to the housing 24 so that the steamer 10 can be disassembled for maintenance and cleaning.

Figure 4:
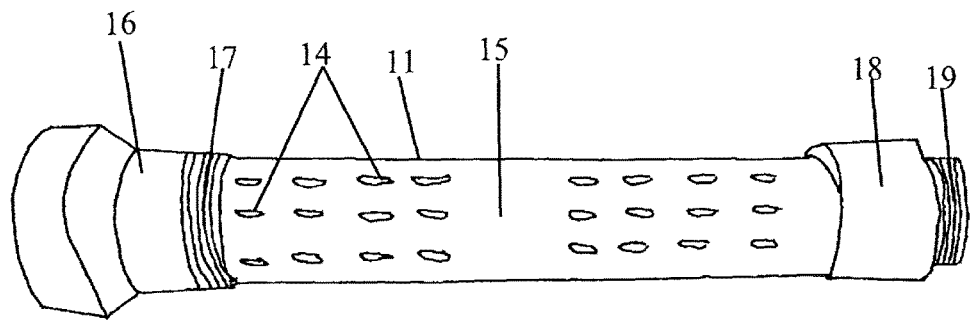
FIG. 4 shows a side perspective view of the core with a spacer positioned on each end of the core.

FIG. 4 shows the core 11 with the spacer 16 positioned on the first end 12 and the spacer 18 positioned on the second opposite end 13. The core 11 is reversibly inserted into these spacers 16 and 18 when the steamer 10 is assembled. The spacers 16 and 18 create a space 30 between the exterior of the core 11 and the interior wall of the housing 24 (see FIG. 8). This space or chamber 30 allows steam entering opening 25 in housing 24 to spread all around the core 11 and to enter all the holes 14 of the core 11 to provide a uniform distribution of steam within the hollow interior 31 of the core 11 (see FIG. 8).

Figure 5:
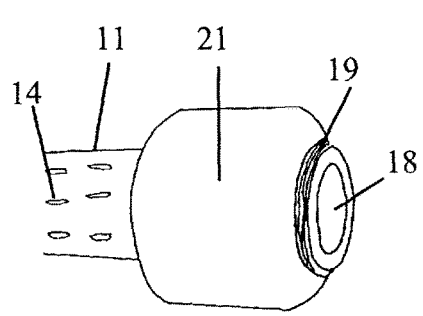
FIG. 5 shows a side side perspective view of a cap positioned over a spacer on a second opposite end of the core
Figure 6:
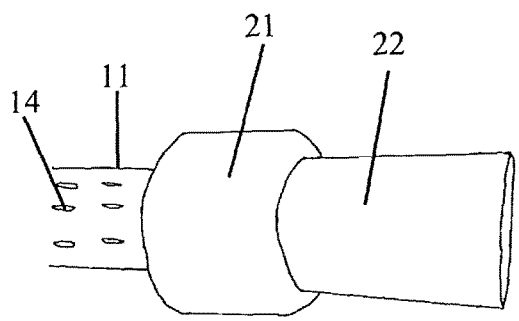
FIG. 6 shows a side perspective view of a locking member which attaches the cap to the spacer at the second opposite end of the core.

FIG. 5 shows an enlarged view of the [21] cap 21 positioned over the spacer 18 at the end 13 of the core 11. The threaded portion 19 of the spacer 18 extends out of the cap 21 so that it can engage the threads 23 of locking member 22. FIG. 6 shows locking member 22 attached to the threaded portion 19, thereby locking the spacer 18 to the cap 21.

Figure 7:
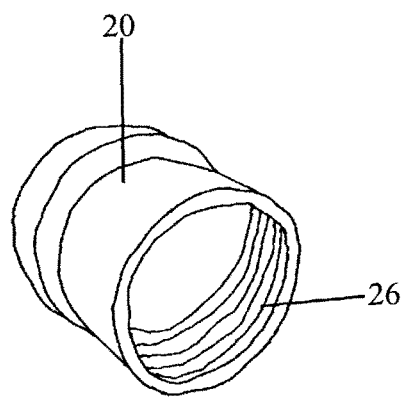
FIG. 7 shows a front side perspective view of a cap for the first end of the housing.

FIG. 7 shows an enlarged view of the cap 20 for the end of the housing near the first end 12 of core 11. The internal threads 26 of the cap 20 engage the external threads 17 of spacer 16 to attach spacer 16 to cap 20.

Figure 8:
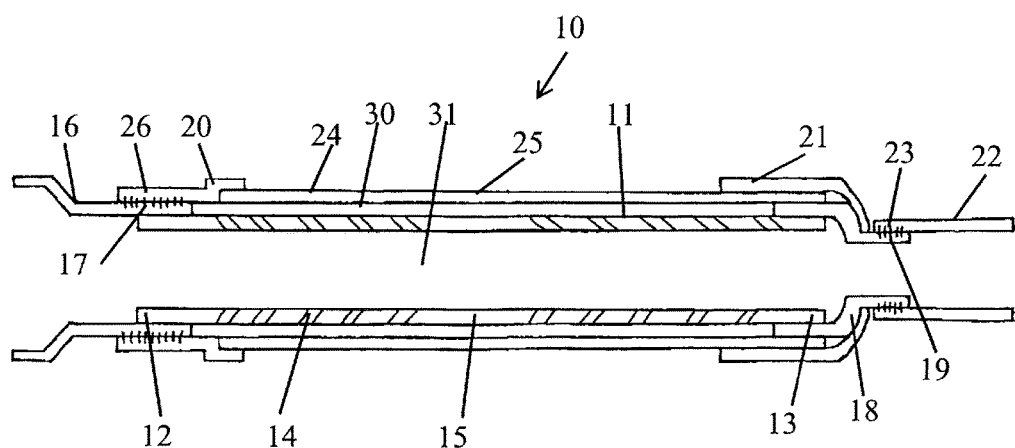
FIG. 8 shows a longitudinal sectional view of the assembled steamer.

FIG. 8 shows a longitudinal sectional view of the assembled steamer 10. Core 11 is reversibly positioned within the interior [30] of the housing 24. First spacer 16 is screwed into cap 20 and cap 20 is reversibly positioned on the housing 24 at one end. Second spacer 18 is reversibly positioned within cap 21 and the threaded portion of second spacer 18 is screwed into the locking member 22. Cap 21 is reversibly positioned onto housing 24 at a second opposite end. End 12 of the core 11 is reversibly positioned within the spacer 16 which centers the core 11 in the interior of housing 24. End 13 of core 11 is reversibly positioned within the spacer 18 which also centers the core 11 in the interior of housing 24. Because the external diameter of the core 11 is smaller than the internal diameter of the housing 24, a chamber 30 is formed around the exterior of core 11. The holes 14 are shown angled relative to the longitudinal axis of the core 11. The angle of the holes 14 will direct the steam in the interior 31 of the core 11 in a desired direction.

In use, a source of steam is attached to the opening 25 in the housing 24. As steam enters housing 24 it enters the chamber 30 and contacts the middle area 15 of core 11, which is opposite opening 25. The middle area 15 can have no holes 14 which will cause the steam to spread around and along the core 11. The steam then enters the openings 14 and fills the hollow interior 31 of the core 11 uniformly. Any object within the hollow interior 31 would, thus, be exposed uniformly to the steam and would be sanitized and decontaminated.

Figures 9A, 9B, 9C:
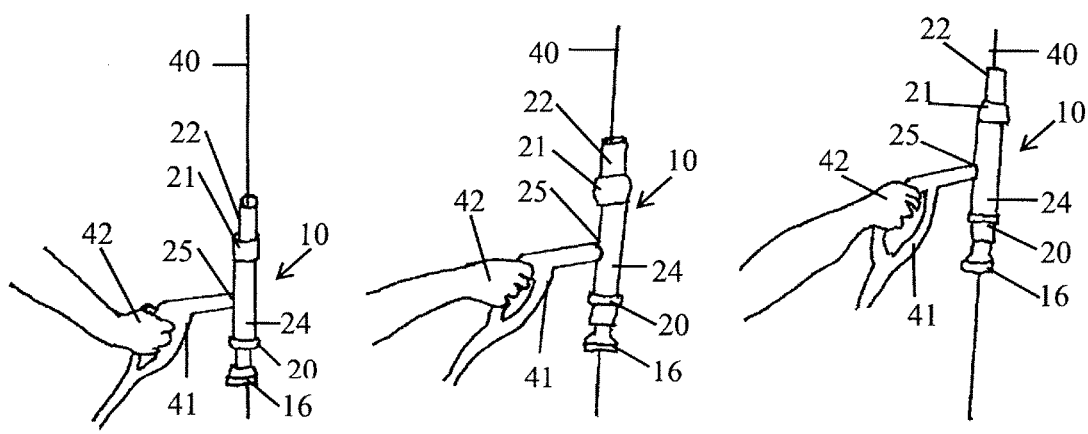
FIG. 9a illustrates a user applying steam to a device with the steamer at one end of the device.
FIG. 9b illustrates a user applying steam to a device with the steamer at a middle portion of the device.
FIG. 9c illustrates a user applying steam to a device with the steamer at a second opposite end of the device.

FIGS. 9a-9c illustrates a user applying steam to a device 40 with the steamer 10. The steamer 10 is attached to the handle 41 of a steam source (not shown). The hand 42 of the user is on the handle 41. The user can use his arm and hand 42 to move the steamer up and down the device 40 to expose the entire device 40 to steam. In FIG. 9a the steamer 10 has a device 40, such as an endoscope, inserted therein. The steamer 10 is positioned at the bottom of the device 40 by the user. In FIG. 9b the steamer 10 is positioned at a middle portion of the device 40. In FIG. 9c the steamer 10 is positioned at the upper end of the device 40. The user can move the steamer 10 back to the position shown in FIG. 9a. The user can move the steamer 10 up and down this way the length of the device 40 as many times as desired to obtain the degree of sanitization and decontamination as desired. A constant flow of steam can be applied to the core 11 and can exit the steamer 10 at either end. The steam can be applied over a sufficient amount of time to sanitize and decontaminate the surface of the device without the rest of the device heating up to a point where the device would be damaged. This feature is particularly valuable when sanitizing and decontaminating medical instruments like endoscopes.

Figure 10:
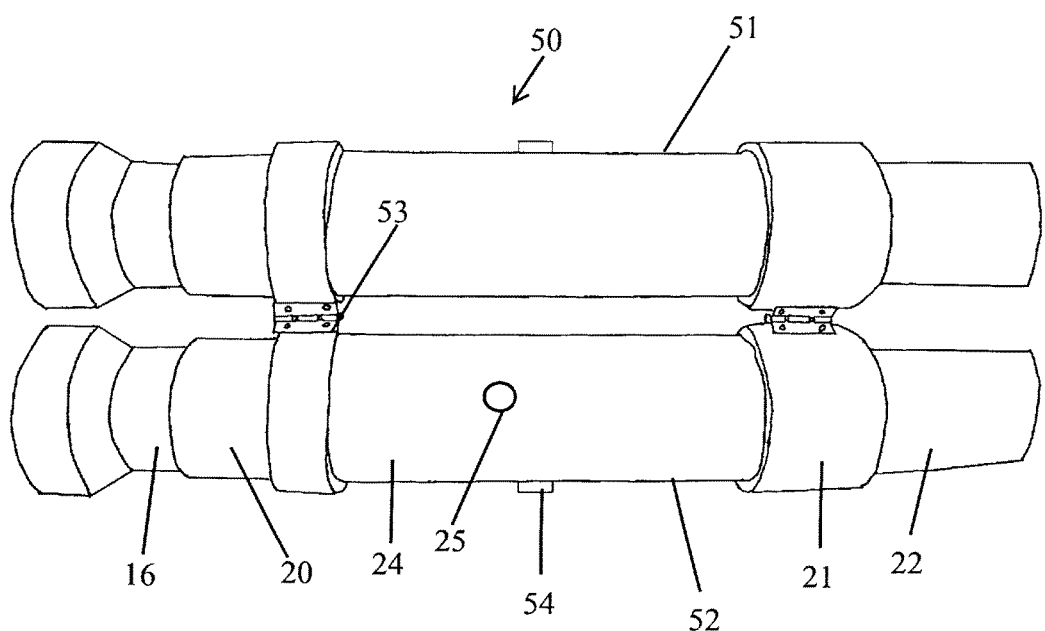
FIG. 10 shows a side perspective exterior view of a hinged embodiment of the steamer in an open position.

FIG. 10 shows a side perspective exterior view of a hinged embodiment 50 of the steamer 10 in an open position. The steamer 10 is divided into a first section 51 and a second section 52 along its length. The sections 51 and 52 are joined with one or more connecting members 53, preferably hinges. The sections 51 and 52 also have a locking mechanism 54. The hinged steamer 50 can be opened, positioned around a device, and then locked closed. The hinged steamer 50 can be removed from the device by unlocking the hinged steamer 50 and opening it. Any type of locking mechanism 54 can be used, preferably magnets.

Any kind of steam generating system can be used with the steamer 10. However, dry vapor steam is preferred wherein the steam is at a temperature of at least 240 $0^F$, preferably 275 $0^F$ to 310 $0^F$. For example, Advanced Vapor Technologies, LLC of Everett, Wash. provides a variety of commercial and residential dry vapor steam generating systems. Another source is AmeriVap Systems, Dawsonville, Ga. Dry vapor steam is steam having a temperature ranging from 240 $0^F$ to 310 $0^F$, a water moisture content of 4% to 6%, and pressure up to 140 PSI.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the steamer can be made of any suitable material such as metal or plastic or a combination thereof. The middle area of the core can also have holes if desired. The holes can be in any desired shape and orientation. Other gases besides steam can be used. The steam can contain additional substances. The parts of the steamer can be attached permanently to each other so that the steamer cannot be disassembled.

We claim:
1. A steamer, comprising:
a) a housing having a first end and a second opposite end and an opening for injecting steam into an interior of said housing;
b) a core having a first end, a second opposite end, and a plurality of holes for receiving said steam into an interior of said core, said core being positioned in said interior of said housing;

c) a first spacer extending to and between said first end of said housing and said first end of said core and a second spacer extending to and between said second opposite end of said housing and said second opposite end of said core, wherein said first spacer and said second spacer center said core within said interior of said housing, thereby forming a chamber in said interior of said housing that extends around an exterior of said core, d) a first pathway extending through said first end of said housing, said second opposite end of said housing, said first end of said core, said second opposite end of said core, said first spacer and said second spacer, and e) a second pathway extending through said opening in said housing and said plurality of holes in said core and into said first pathway, f) wherein, when the steamer is fully assembled and in use, said housing, said first pathway, said first spacer, said second spacer and said core are arranged for allowing said steam to travel along said second pathway into said interior of said core and exit said steamer along said first pathway and simultaneously out through said first end of said housing, said second opposite end of said housing, said first end of said core and said second opposite end of said core and allowing an item for steaming to travel along said first pathway and simultaneously through said first end of said housing, said second opposite end of said housing, said first end of said core and said second opposite end of said core.

2. The steamer of claim 1, further comprising a first cap at said first end of said housing and a second cap at said second opposite end of said housing, wherein said first end of said housing is coupled to and between the first cap and the first spacer.

3. The steamer of claim 1, further comprising a steam source coupled to said opening in said housing capable of producing a constant flow if steam.

4. The steamer of claim 2, further comprising said one of said spacers being attached to said cap at said first end of said housing by means of threads and said another of said spacers being attached to said cap at said second opposite end of said housing by means of a threaded locking member.

5. The steamer of claim 1, wherein the item is an endoscope.

6. The steamer of claim 1, further comprising said core having a middle area opposite said opening in said housing, wherein said middle area has no holes for receiving steam into said interior of said core.

7. The steamer of claim 1, further comprising said steamer being constructed in two segments wherein said two segments are joined by one or more connecting members so that said steamer can be opened and closed along its length.

8. A steamer, comprising:
a) a housing having a first end, a second opposite end, a first pathway extending through the first end of the housing and the second opposite end of the housing and configured for receiving an item for steaming through both the first end of the housing and the second opposite end of the housing and an opening for injecting steam into an interior of said housing;

b) a core having a first end and a second opposite end and a plurality of holes for receiving said steam into an interior of said core, said core being positioned in said interior of said housing, wherein said holes are oriented at an angle relative to a longitudinal axis of said core, wherein said first pathway extends through said first end of said core and said second opposite end of said core, and wherein said core is configured for receiving said item for steaming through both said first end of said core and said second opposite end of said core;

c) spacers centering said core within said interior of said housing, thereby forming a chamber in said interior of said housing around an exterior of said core, wherein said first pathway extends through said spacers;

d) a cap at said first end of said housing and a cap at said second opposite end of said housing, one of said spacers being reversibly attached to said cap at said first end of said housing and another of said spacers being reversibly attached to said cap at said second opposite end of said housing, wherein said first pathway extends through said cap at said first end of said housing and said cap at said second opposite end of said housing; and e) said one of said spacers fitting reversibly over said first end of said core and said another of said spacers fitting reversibly over said second opposite end of said core, f) wherein, when the steamer is fully assembled and in use, said housing, said first pathway, said cap at said first end of said housing, said cap at said second opposite end of said housing and said core are configured for allowing said steam to exit the steamer along said first pathway and simultaneously out through said first end of said housing, said second opposite end of said housing, said cap at said first end of said housing, said cap at said second opposite end of said housing, said first end of said core and said second opposite end of said core and allowing said item for steaming to travel along said first pathway and through said first end of said housing, said second opposite end of said housing, said first end of said core and said second opposite end of said core.

9. The steamer of claim 8, further comprising said one of said spacers being attached to said cap at said first end of said housing by means of threads and said another of said spacers being attached to said cap at said second opposite end of said housing by means of a threaded locking member.

10. The steamer of claim 8, further comprising said core having a middle area opposite said opening in said housing, wherein said middle area has no holes for receiving steam into said interior of said core.

11. The steamer of claim 8, further comprising said steamer being constructed in two segments wherein said two segments are joined by one or more connecting members so that said steamer can be opened and closed along its length.

12. A steamer comprising:
an elongate housing including a housing sidewall, a first end defining a first housing opening, a second opposite end defining a second housing opening, and a steam injection opening extending through the housing sidewall, an elongate core positioned in the housing, the core including a core sidewall defining a first pathway having a longitudinal axis, a plurality of holes through the core sidewall, a first end defining a first core opening, and a second opposite end defining a second core opening, wherein the longitudinal axis extends through the first housing opening, the second housing opening, the first core opening and the second core opening, a chamber defined between the housing sidewall and the core sidewall, the chamber having a first end and a second opposite end, a first spacer extending to and between the first end of the housing and the first end of the core, the first spacer encircling the core and defining the first end of the chamber, and a second spacer extending to and between the second opposite end of the housing and the second opposite end of the core, the second spacer encircling the core and defining the second opposite end of the chamber, wherein, when the steamer is fully assembled and in use steaming an item, the first pathway extends through the first housing opening, the second housing opening, the first core opening and the second core opening.

13. The steamer of claim 12 wherein the first pathway is configured for directing steam out of the steamer simultaneously through the first housing opening, the second housing opening, the first core opening and the second core opening.

14. The steamer of claim 12 wherein the first pathway does not open into the chamber through either the first core opening or the second core opening.

15. The steamer of claim 12 including a steam source operatively coupled to the steam injection opening, the steam source being configured for producing a constant flow of steam to the steamer.

16. The steamer of claim 12 wherein the first end of the housing is coupled to and between a first cap and the first spacer.

17. The steamer of claim 16 wherein the second spacer is coupled to and between a second cap and the second opposite end of the core.

18. The steamer of claim 12 wherein, when the steamer is fully assembled and in use steaming the item, the steamer has a length terminating at each end thereof in an exit opening through which the longitudinal axis of the first pathway extends, each exit opening configured to allow the passage of steam out of the steamer.

19. The steamer of claim 12 wherein, when the steamer is fully assembled and in use steaming the item, the first pathway extends out of a distal-most end and a proximal-most end of the steamer.

20. A steamer comprising,
an elongate body terminating at each end thereof in an opening through which steam and an item for steaming can pass, the body including,
a first tube that is open at each end thereof,
a second tube concentrically arranged around the first tube,
a pathway extending along a longitudinal axis defined by the first tube,
a chamber defined between the first tube and the second tube and closed at each end thereof,
a steam injection opening extending through the second tube and into the chamber,
a plurality of openings extending through a sidewall of the first tube which fluidly couple the chamber to the pathway,
wherein, when the steamer is fully assembled for steaming the item, the pathway extends uninterrupted through each open end of the first tube and out of the steamer through each end of the body.

\* \* \* \* \*